US012702315B2

(12) United States Patent
Sztuk et al.

(10) Patent No.: US 12,702,315 B2
(45) Date of Patent: Aug. 11, 2026

(54) HEALTH NOTIFICATIONS FROM EYE MEASUREMENTS

(71) Applicant: Meta Platforms Technologies, LLC, Menlo Park, CA (US)

(72) Inventors: Sebastian Sztuk, Menlo Park, CA (US); Salvael Ortega Estrada, Redmond, WA (US)

(73) Assignee: Meta Platforms Technologies, LLC, Menlo Park, CA (US)

( * ) Notice: Subject to any disclaimer, the term of this patent is extended or adjusted under 35 U.S.C. 154(b) by 1047 days.

(21) Appl. No.: 17/591,542

(22) Filed: Feb. 2, 2022

(65) Prior Publication Data

US 2025/0248609 A1 Aug. 7, 2025

(51) Int. Cl.
*A61B 5/024* (2006.01)
*A61B 3/113* (2006.01)
(Continued)

(52) U.S. Cl.
CPC .............. *A61B 5/024* (2013.01); *A61B 3/113* (2013.01); *A61B 3/1233* (2013.01); *A61B 3/14* (2013.01);
(Continued)

(58) Field of Classification Search
CPC ........... A61B 3/113; A61B 3/10; A61B 5/742; A61B 5/0022; A61B 3/0025; A61B 3/08; A61B 3/085; A61B 5/0013; A61B 5/0075; A61B 5/0077; A61B 5/0086; A61B 5/0088; A61B 5/0091; A61B 5/0261; A61B 5/1114; A61B 5/14532; A61B 5/14546; A61B 5/1455; A61B 5/163; A61B 5/168; A61B 5/4088; A61B 5/4547; A61B 5/6801; A61B 5/7203; A61B 5/7257; A61B 5/7405; A61B 5/0048; A61B 5/1122; A61B 5/1124; A61B 5/1128; A61B 5/1176; A61B 5/14542; A61B 5/682; A61B 5/6887;
(Continued)

(56) References Cited

U.S. PATENT DOCUMENTS 11,205,069 B1 * 12/2021 Sharma ................ G06V 10/143
2013/0241907 A1 * 9/2013 Amirparviz ........ G02B 27/0093
345/207

(Continued)

FOREIGN PATENT DOCUMENTS

CN 202210900796 * 11/2022 ............. G06F 21/32
WO WO 2021230559 * 11/2021 ........... H04N 23/695
WO WO-2021230559 A1 * 11/2021 ............. G06F 3/013

OTHER PUBLICATIONS

International Preliminary Report on Patentability for International Application No. PCT/US2023/012195, mailed Aug. 15, 2024, 11 pages.

(Continued)

*Primary Examiner* — Brandi N Thomas
(74) *Attorney, Agent, or Firm* — Potomac Law Group, PLLC; Dannon G. Allbee

(57) ABSTRACT

Eye data is captured with one or more sensors of a head mounted device. The one or more sensors are configured to sense an eyebox region. A differential value is generated by comparing the eye data to previous data. A user notification is generated in response to the differential value reaching an outlier threshold value.

20 Claims, 9 Drawing Sheets

(51) Int. Cl.
*A61B 3/12* (2006.01)
*A61B 3/14* (2006.01)
*A61B 5/00* (2006.01)
*G02B 27/00* (2006.01)

(52) U.S. Cl.
CPC ........ *A61B 5/0022* (2013.01); *G02B 27/0093* (2013.01)

(58) Field of Classification Search
CPC ... A61B 5/6898; A61B 5/7264; A61B 5/7455; A61B 2562/0233; A61B 2562/0238; A61B 2562/146; A61B 2576/02; A61B 5/0024; A61B 5/6814; A61B 5/7275; G02B 27/0093; G02B 30/24; G16H 50/30; G16H 50/20; G16H 20/00; G16H 30/20; G16H 30/40; G16H 40/67; G16H 10/20; G16H 10/60; G16H 20/70; G16H 50/50; G16H 50/70
See application file for complete search history.

(56) References Cited

U.S. PATENT DOCUMENTS

2015/0326570 A1* 11/2015 Publicover .............. G06F 3/017 382/117
2018/0164882 A1* 6/2018 Johnson ................ G02F 1/0063
2018/0286070 A1* 10/2018 Benedetto ................. G06T 7/62
2018/0330302 A1* 11/2018 Peterson ................. G10L 25/66
2020/0214559 A1 7/2020 Krueger et al.
2022/0160223 A1* 5/2022 Bradley ............. G02B 27/0176

OTHER PUBLICATIONS

International Search Report and Written Opinion for International Application No. PCT/US2023/012195, mailed May 4, 2023, 12 pages.

* cited by examiner

NOTIFICATION IN RESPONSE TO EYE DATA

CONCUSSION NOTIFICATION IN RESPONSE TO PUPIL SIZE

HEALTH NOTIFICATIONS FROM EYE MEASUREMENTS

TECHNICAL FIELD

This disclosure relates generally to optics, and in particular to head mounted devices.

BACKGROUND INFORMATION

A head mounted device is a wearable electronic device, typically worn on the head of a user. Head mounted devices may include one or more electronic components for use in a variety of applications, such as gaming, aviation, engineering, medicine, entertainment, activity tracking, and so on. Head mounted devices may include display to present virtual images to a wearer of the head mounted device. When a head mounted device includes a display, it may be referred to as a head mounted display (HMD). Head mounted devices may include sensors to capture data from an eyebox region.

BRIEF DESCRIPTION OF THE DRAWINGS

Non-limiting and non-exhaustive embodiments of the invention are described with reference to the following figures, wherein like reference numerals refer to like parts throughout the various views unless otherwise specified.

DETAILED DESCRIPTION

Figure 1:
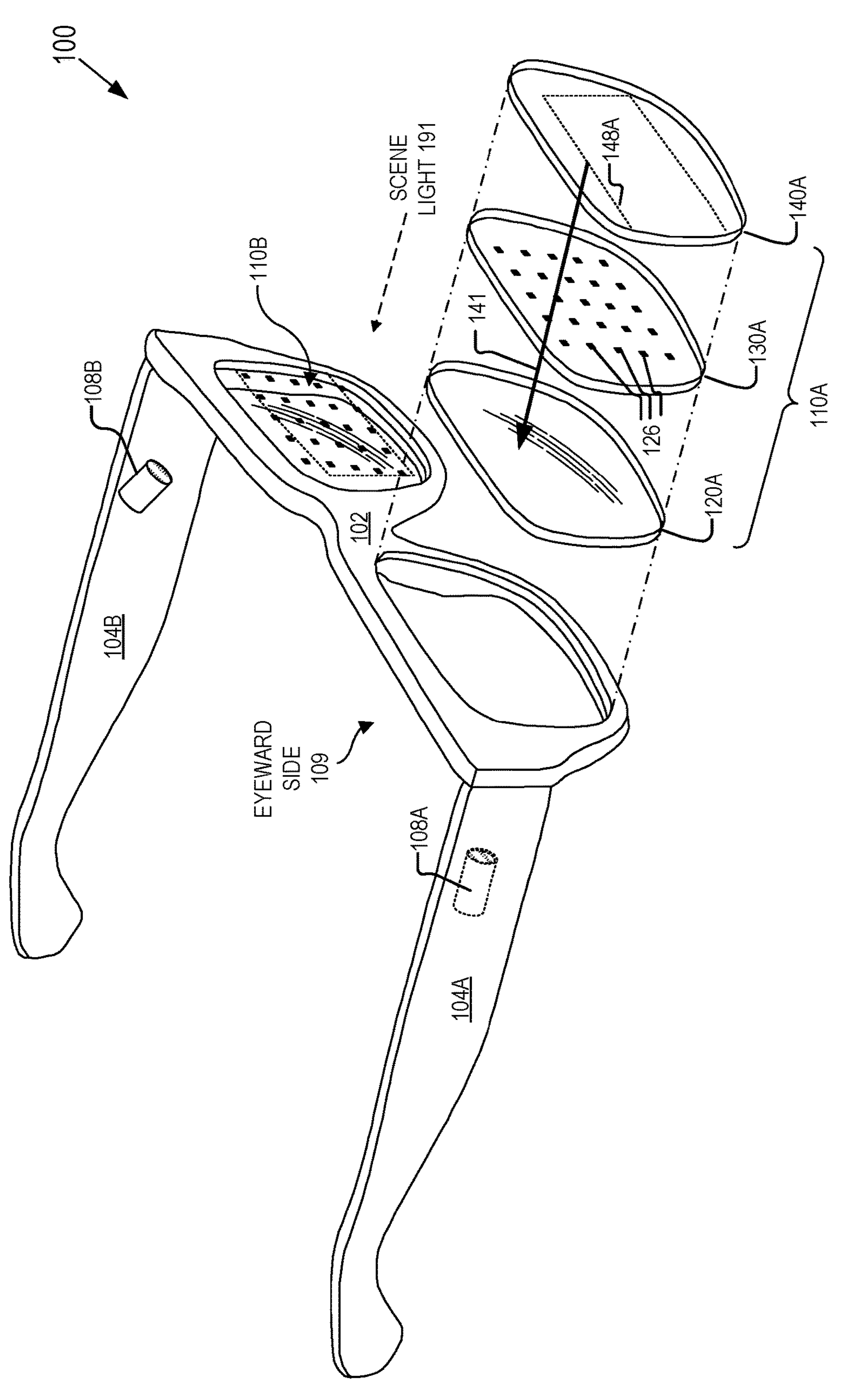
FIG. 1 illustrates an example head mounted device, in accordance with aspects of the disclosure.

Embodiments of generating health notifications from eye measurements are described herein. In the following description, numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

In some implementations of the disclosure, the term "near-eye" may be defined as including an element that is configured to be placed within 50 mm of an eye of a user while a near-eye device is being utilized. Therefore, a "near-eye optical element" or a "near-eye system" would include one or more elements configured to be placed within 50 mm of the eye of the user.

In aspects of this disclosure, visible light may be defined as having a wavelength range of approximately 380 nm-700 nm. Non-visible light may be defined as light having wavelengths that are outside the visible light range, such as ultraviolet light and infrared light. Infrared light having a wavelength range of approximately 700 nm-1,000,000 nm includes near-infrared light. In aspects of this disclosure, near-infrared light may be defined as having a wavelength range of approximately 700 nm-1600 nm.

In aspects of this disclosure, the term "transparent" may be defined as having greater than 90% transmission of light. In some aspects, the term "transparent" may be defined as a material having greater than 90% transmission of visible light.

Implementations of devices, systems, and methods of operating a head mounted device in response to eye data are disclosed herein. Eye data of a user of a head mounted device may be captured by sensors of the head mounted device. The sensors may include image sensors, photodiodes, micro-electro-mechanical systems (MEMS) mirrors, ultrasound, or LIDAR units, for example. The eye data may include one or more images of the eye, a position of the eye, a measurement of the eye (e.g. pupil size), and/or a measurement of the eye over time (e.g. speed of pupil dilation). If the eye data reaches an outlier threshold value, a user notification is generated. In a specific illustration, a pupil size of an eye of a user is measured using an eye-tracking system. If the pupil size of the eye is much larger than previous pupil sizes (previous eye data) of the same user for an extended period of time, a concussion notification is generated. The notification may be included in a virtual image presented to the user by the head mounted device. In other implementations, the concussion notification may be sent to a third party such as a coach, parent, and/or medical provider. These and other embodiments are described in more detail in connection with FIGS. 1-8.

FIG. 1 illustrates an example head mounted device 100, in accordance with aspects of the present disclosure. The illustrated example of head mounted device 100 is shown as including a frame 102, temple arms 104A and 104B, and near-eye optical elements 110A and 110B. Cameras 108A and 108B are shown as coupled to temple arms 104A and 104B, respectively. Cameras 108A and 108B may be configured to image an eyebox region to image the eye of the user to capture eye data of the user. Cameras 108A and 108B may image the eyebox region directly or indirectly. For example, optical elements 110A and/or 110B may have an optical combiner that is configured to redirect light from the eyebox to the cameras 108A and/or 108B. In some implementations, near-infrared light sources (e.g. LEDs or vertical-cavity side emitting lasers) illuminate the eyebox region with near-infrared illumination light and cameras 108A and/or 108B are configured to capture infrared images. Cameras 108A and/or 108B may include complementary metal-oxide semiconductor (CMOS) image sensor. A near-infrared filter that receives a narrow-band near-infrared wavelength may be placed over the image sensor so it is sensitive to the narrow-band near-infrared wavelength while rejecting visible light and wavelengths outside the narrow-band. The near-infrared light sources may emit the narrow-band wavelength that is passed by the near-infrared filters.

In addition to image sensors, various other sensors of head mounted device 100 may be configured to capture eye data. Ultrasound or LIDAR chips may be configured in frame 102 to detect a position of an eye of the user by detecting the position of the cornea of the eye, for example. Discrete photodiodes included in frame 102 or optical elements 110A and/or 110B may also be used to detect a position of the eye of the user. Discrete photodiodes may be used to detect "glints" of light reflecting off of the eye, for example. Eye data generated by various sensors may not necessarily be considered "images" of the eye.

FIG. 1 also illustrates an exploded view of an example of near-eye optical element 110A. Near-eye optical element 110A is shown as including an optically transparent layer 120A, an illumination layer 130A, and a display layer 140A. Display layer 140A may include a waveguide 148 that is configured to direct virtual images included in visible image light 141 to an eye of a user of head mounted device 100 that is in an eyebox region of head mounted device 100. In some implementations, at least a portion of the electronic display of display layer 140A is included in the frame 102 of head mounted device 100. The electronic display may include an LCD, an organic light emitting diode (OLED) display, micro-LED display, pico-projector, or liquid crystal on silicon (LCOS) display for generating the image light 141.

When head mounted device 100 includes a display, it may be considered a head mounted display. Head mounted device 100 may be considered an augmented reality (AR) head mounted display. While FIG. 1 illustrates a head mounted device 100 configured for augmented reality (AR) or mixed reality (MR) contexts, the disclosed embodiments may also be used in other implementations of a head mounted display such as virtual reality head mounted displays. Additionally, some implementations of the disclosure may be used in a head mounted device that do not include a display.

Illumination layer 130A is shown as including a plurality of in-field illuminators 126. In-field illuminators 126 are described as "in-field" because they are in a field of view (FOV) of a user of the head mounted device 100. In-field illuminators 126 may be in a same FOV that a user views a display of the head mounted device 100, in an embodiment. While in-field illuminators 126 may introduce minor occlusions into the near-eye optical element 110A, the in-field illuminators 126, as well as their corresponding electrical routing may be so small as to be unnoticeable or insignificant to a wearer of head mounted device 100. Each in-field illuminator 126 may be disposed on a transparent substrate and may be configured to emit light to an eyebox region on an eyeward side 109 of the near-eye optical element 110A. In some aspects of the disclosure, the in-field illuminators 126 are configured to emit near infrared light (e.g. 750 nm-1.6 μm). Each in-field illuminator 126 may be a micro light emitting diode (micro-LED), an edge emitting LED, a vertical cavity surface emitting laser (VCSEL) diode, or a Superluminescent diode (SLED). In some implementations, illuminators 126 are not in-field. Rather, illuminators 126 could be out-of-field in some implementations.

As shown in FIG. 1, frame 102 is coupled to temple arms 104A and 104B for securing the head mounted device 100 to the head of a user. Example head mounted device 100 may also include supporting hardware incorporated into the frame 102 and/or temple arms 104A and 104B. The hardware of head mounted device 100 may include any of processing logic, wired and/or wireless data interface for sending and receiving data, graphic processors, and one or more memories for storing data and computer-executable instructions. In one example, head mounted device 100 may be configured to receive wired power and/or may be configured to be powered by one or more batteries. In addition, head mounted device 100 may be configured to receive wired and/or wireless data including video data.

FIG. 1 illustrates near-eye optical elements 110A and 110B that are configured to be mounted to the frame 102. In some examples, near-eye optical elements 110A and 110B may appear transparent or semi-transparent to the user to facilitate augmented reality or mixed reality such that the user can view visible scene light from the environment while also receiving image light 141 directed to their eye(s) by way of display layer 140A. In further examples, some or all of near-eye optical elements 110A and 110B may be incorporated into a virtual reality headset where the transparent nature of the near-eye optical elements 110A and 110B allows the user to view an electronic display (e.g., a liquid crystal display (LCD), an organic light emitting diode (OLED) display, or micro-LED display, etc.) incorporated in the virtual reality headset.

Optically transparent layer 120A is shown as being disposed between the illumination layer 130A and the eyeward side 109 of the near-eye optical element 110A. The optically transparent layer 120A may receive the infrared illumination light emitted by the illumination layer 130A and pass the infrared illumination light to illuminate the eye of the user. As mentioned above, the optically transparent layer 120A may also be transparent to visible light such as scene light received from the environment and/or image light 141 received from the display layer 140A. In some examples, the optically transparent layer 120A has a curvature for focusing light (e.g., display light and/or scene light) to the eye of the user. Thus, the optically transparent layer 120A may, in some examples, may be referred to as a lens. In some aspects, the optically transparent layer 120A has a thickness and/or curvature that corresponds to the specifications of a user. In other words, the optically transparent layer 120A may be a prescription lens. However, in other examples, the optically transparent layer 120A may be a non-prescription lens.

Figure 2A:
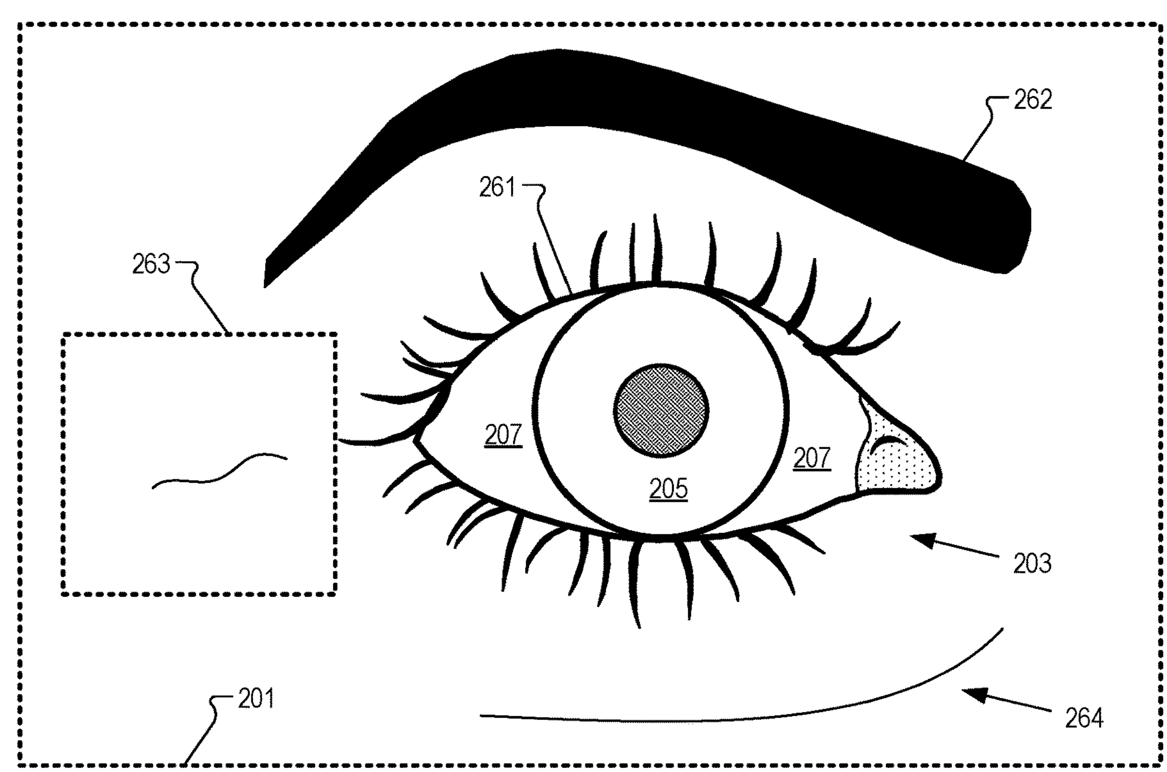
FIGS. 2A-2F illustrate various features, positions, and measurements of an eye and an eyebox region that may be included in eye data, in accordance with aspects of the disclosure.
Figure 2B:
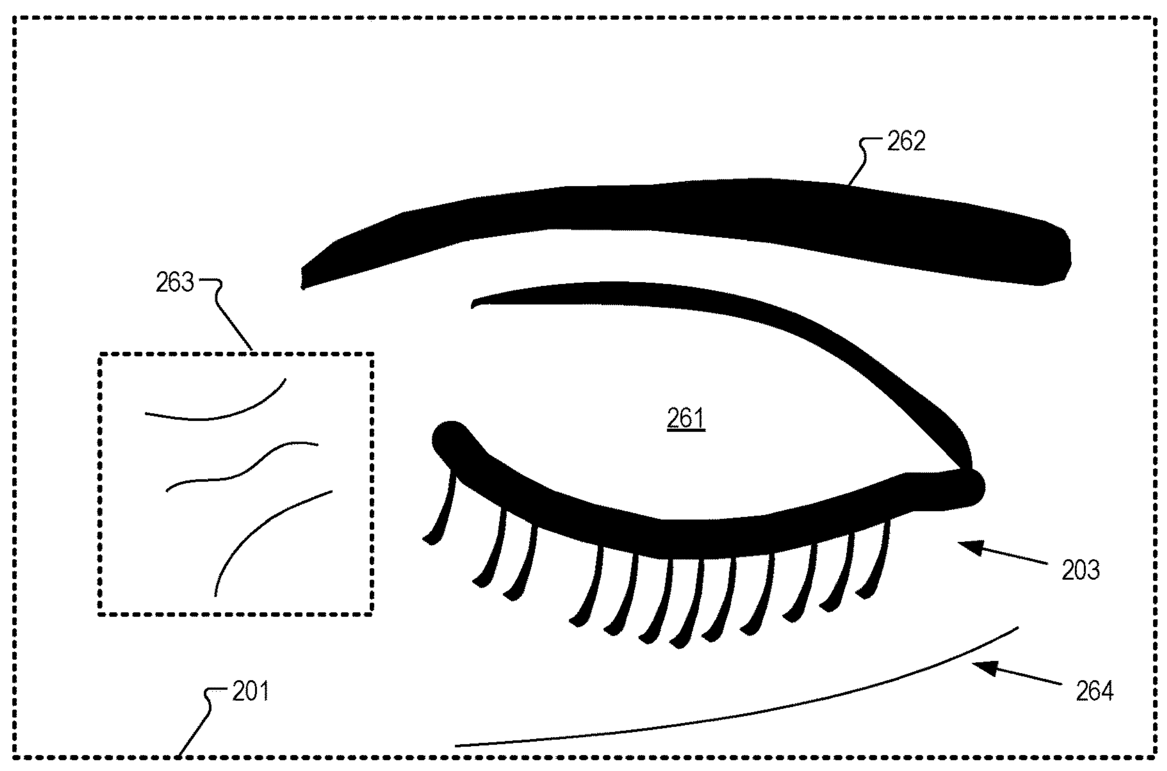

FIGS. 2A and 2B illustrate an eye 203 in an eyebox region 201, in accordance with implementations of the disclosure. FIG. 2A illustrates eye 203 that is open and FIG. 2B illustrates eye 203 shut. Eye data of eye 203 may include a position of eye 203, a measurement of the eye 203 (e.g. pupil size), and/or a measurement of the eye over time (e.g. speed of pupil dilation). The eye data may also include a movement and/or shape of eyebrows 262, movement and/or shape of eyelid 261, and/or facial micro gestures associate with skin lines for example. Eye 203 may be wide open, shut, or any variation in between. In some contexts, eye 203 may be squinting.

In FIG. 2A, most of the iris 205 and large portions of the sclera 207 are visible. When eye 203 is squinting, less of iris 205 and sclera 207 will be visible. In FIG. 2B, neither iris 205 nor sclera 207 are visible. In FIG. 2A, eyebrow 262 is arched. In FIG. 2B, eyebrow 262 is flattened and closer to eye 203 than in FIG. 2A. Similarly, smile line 264 is flattened in FIG. 2B compared to the more arched smile line 264 in FIG. 2A. FIG. 2B also illustrates an increased number of lines in corner region 263 compared to the lines in corner region 263 of FIG. 2A. The shape and or number of lines in corner region 263 may correspond to micro gestures, squinting, cringing, eye strain, and/or user discomfort, for example. Therefore, detecting the size, shape, or quantity of various eye features in eyebox region 201 provides eye data that can be indicative of a user reaction or adaptation to a particular environmental context.

Figures 2C, 2D, 2E, 2F:
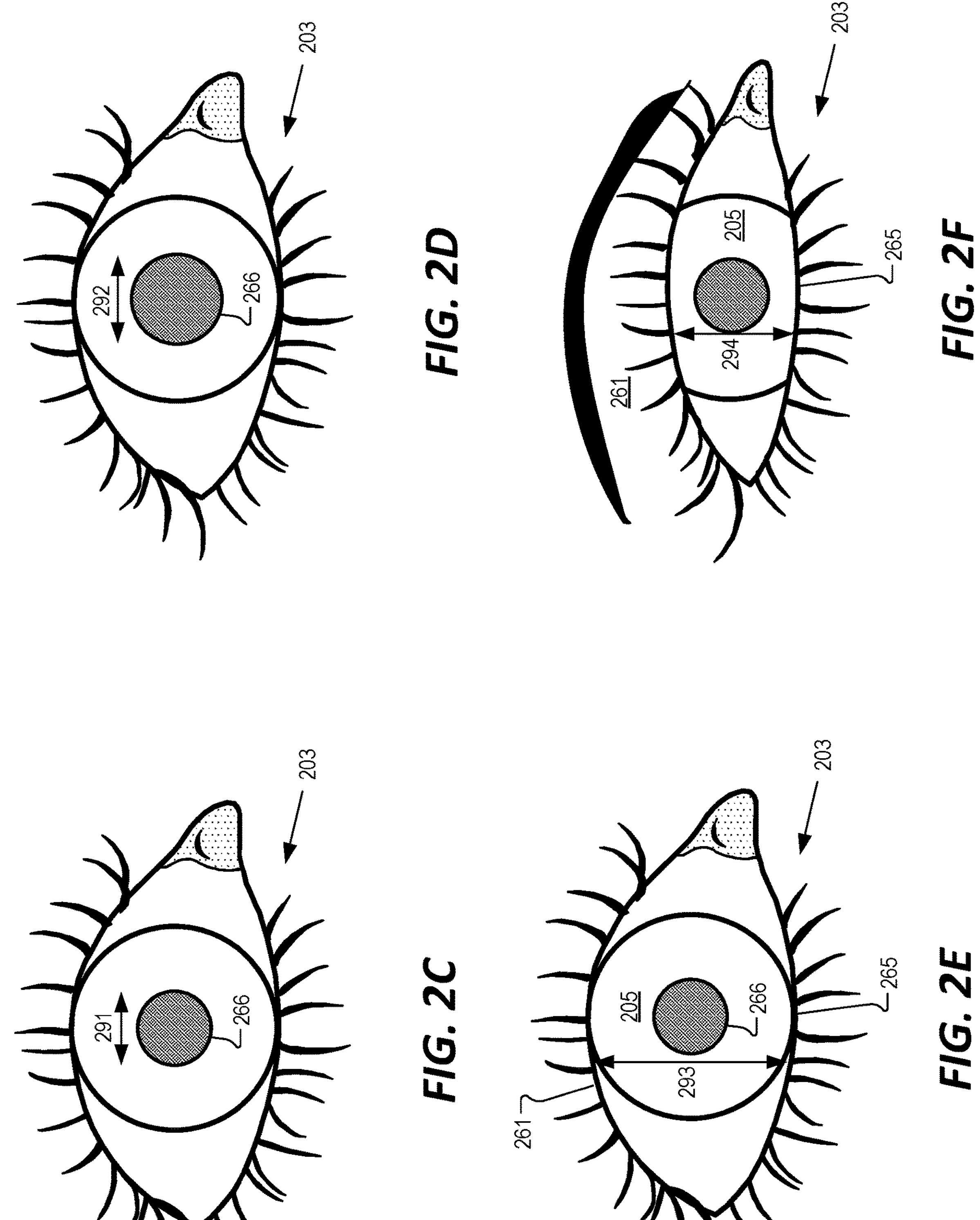

FIG. 2C illustrates eye 203 having a pupil 266 with a diameter of dimension 291. FIG. 2D illustrates eye 203 having a pupil 266 with a diameter of dimension 292 that is larger than dimension 291. In some implementations of the disclosure, eye data may include the size (e.g. diameter) of pupil 266. In some implementations of the disclosure, eye data may include the size (e.g. diameter) of pupil 266 over a particular time period. Thus, when the size of pupil 266 is captured over a plurality of time periods, the speed of pupil dilation may be determined.

FIGS. 2E and 2F illustrate another example measurement of eye 203 that may be included in eye data, in accordance with implementations of the disclosure. For example, the dimension 293 of iris 205 between top eyelid 261 and bottom eye lid 265 is larger in FIG. 2E when compared to the dimension 294 of iris 205 when eye 203 is squinting in FIG. 2F.

Figure 3C:
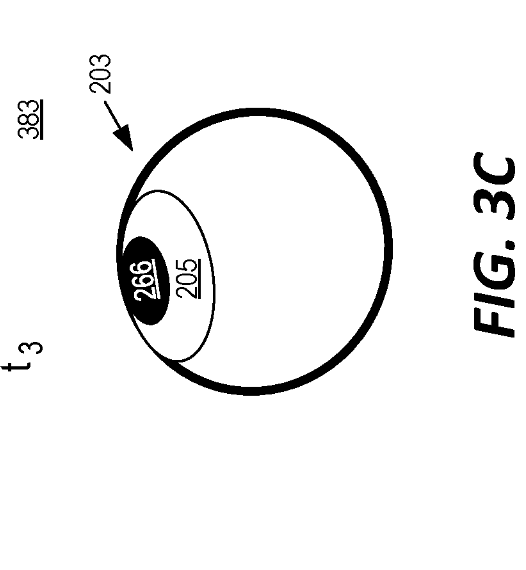
FIGS. 3A-3C illustrates different positions of an eye at different times, in accordance with aspects of the disclosure.
Figure 3B:
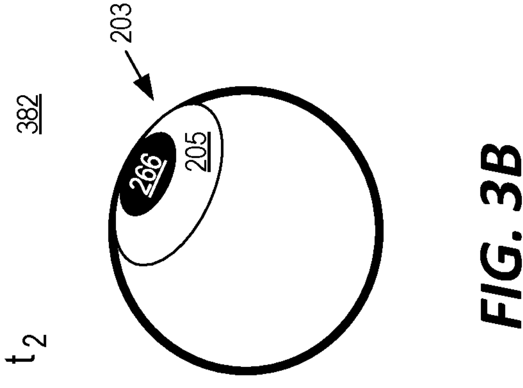
Figure 3A:
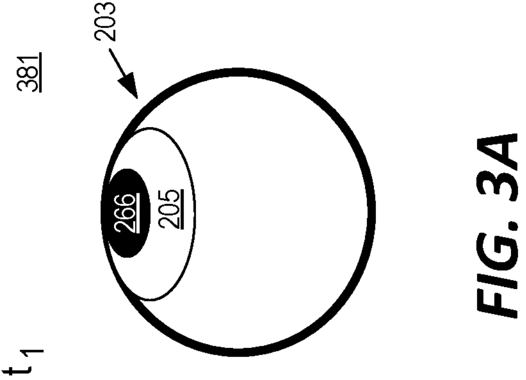

FIGS. 3A-3C illustrates different positions of eye 203 at different times, in accordance with implementations of the disclosure. FIG. 3A illustrates eye 203 in a centered position 381 at a time $t_1$. Centered position 381 may be associated with eye 203 looking straight forward at an object in the far field (e.g. focus distance of infinity). FIG. 3B illustrates eye 203 in a right-of-center position 382 at a time $t_2$. FIG. 3C illustrates eye 203 in a slightly-left-of-center position 383 at a time $t_3$. The position of eye 203 may be determined by tracking the position of pupil 266, iris 205, tracking the cornea (not specifically illustrated), and/or other suitable eye-tracking techniques. Thus, eye data may include a position of eye 203 and/or positions of eye 203 over time. The speed of a position change of eye 203 may be included in eye data. For example, if eye 203 goes from position 381 to position 382 very quickly (e.g. within 200 ms), this movement may be considered a saccade. Smaller movements of eye 203 in short time periods may be considered micro-saccades. The number of saccades or micro-saccades in a particular time period may be counted using image processing techniques or other suitable pupil position techniques. The number of saccades or micro-saccades in a particular time period may be included in eye data, in various implementations of the disclosure. The position changes of eye 203 may be considered gaze flickering where eye 203 changes position often but does not change position rapidly enough to be considered a saccade or micro-saccade. Gaze flickering may be a sign of discomfort due to ambient light brightness or display brightness. Squinting or squinting in combination with pupil dilation and gaze flicking may also be a sign of discomfort.

Figure 4:
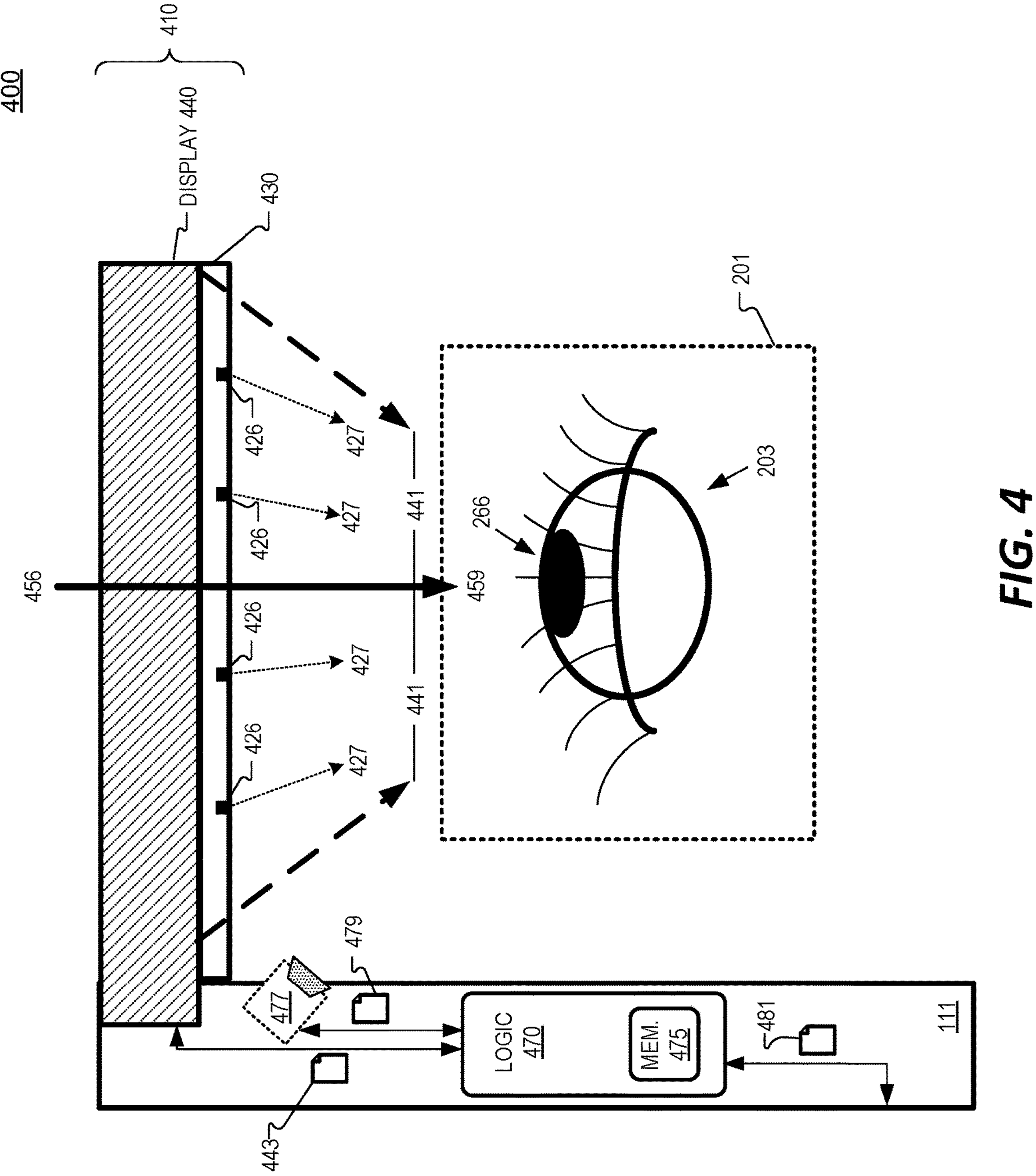
FIG. 4 illustrates a top view of a portion of an example head mounted device that may generate notifications from eye data, in accordance with aspects of the disclosure.

FIG. 4 illustrates a top view of a portion of an example head mounted device 400, in accordance with implementations of the disclosure. The illustration of FIG. 4 illustrates a schematic for capturing eye data from a left eyebox region. Of course, a second half of the head mounted device 400 may include a similar system to image a right eyebox region. Head mounted device 400 may include a display layer 440 and an illumination layer 430. All or a portion of display layer 440 may be transparent or semi-transparent to allow scene light 456 from an external environment to become incident on eye 203 so that a user can view their external environment in addition to viewing virtual images presented in image light 441. Additional optical layers (not specifically illustrated) may also be included in example optical element 410. For example, a focusing lens layer may optionally be included in optical element 410 to focus scene light 456 and/or virtual images included in image light 441 generated by display layer 440.

Illumination layer 430 includes light sources 426 configured to illuminate an eyebox region 201 with infrared illumination light 427. Illumination layer 430 may include a transparent refractive material that functions as a substrate for light sources 426. Infrared illumination light 427 may be near-infrared illumination light. Camera 477 is configured to image (directly) eye 203, in the illustrated example of FIG. 4. In other implementations, camera 477 may (indirectly) image eye 203 by receiving reflected infrared illumination light from an optical combiner layer (not illustrated) included in optical element 410. The optical combiner layer may be configured to receive reflected infrared illumination light (the infrared illumination light 427 reflected from eyebox region 201) and redirect the reflected infrared illumination light to camera 477. In this implementation, camera 477 would be oriented to receive the reflected infrared illumination light from the optical combiner layer of optical element 410.

Camera 477 may include a CMOS image sensor, in some implementations. An infrared filter that receives a narrow-band infrared wavelength may be placed over the image sensor so it is sensitive to the narrow-band infrared wavelength while rejecting visible light and wavelengths outside the narrow-band. Infrared light sources (e.g. light sources 426) such as infrared LEDs or infrared VCSELS that emit the narrow-band wavelength may be oriented to illuminate eye 203 with the narrow-band infrared wavelength. Camera 477 may capture eye-tracking images of eyebox region 201.

Light sources 426 and camera 477 are merely an example eye-tracking system configuration and other suitable eye-tracking systems and techniques may also be used to capture eye data, in implementations of the disclosure. In an implementation, a MEMS mirror-based RGB laser system is used for capturing eye data. Other sensors of a head mounted device (not specifically illustrated) for capturing eye data may include photodiodes, ultrasound, or LIDAR units, for example. Eyebox region 201 may include eye 203 as well as surrounding features in an ocular area such as eyebrows, eyelids, eye lines, etc.

Processing logic 470 may initiate one or more image captures with camera 477 and camera 477 may provide eye data 479 (that may include eye-tracking images) to processing logic 470. Processing logic 470 may perform image processing to determine the size and/or position of various features of the eyebox region 201. For example, processing logic 470 may be configured to determine size and/or position of the features described in association with FIGS. 2A-3C. Processing logic 470 may perform image processing to determine a pupil position or pupil size of pupil 266. Processing logic 470 may perform image processing to determine saccade and/or micro-saccade events over a fixed time period. Additional techniques are described below with respect to FIGS. 5 and 7.

In the illustrated implementation of FIG. 4, a memory 475 is included in processing logic 470. In other implementations, memory 475 may be external to processing logic 470. In some implementations, memory 475 is located remotely from processing logic 470. In implementations, virtual image(s) are provided to processing logic 470 for presentation in image light 441. In some implementations, virtual images are stored in memory 475. Processing logic 470 may be configured to receive virtual images from a local memory or the virtual images may be wirelessly transmitted to the head mounted device 400 and received by a wireless interface (not illustrated) of the head mounted device.

Display layer 440 presents virtual images in image light 441 to an eyebox region 201 for viewing by an eye 203. Processing logic 470 is configured to drive virtual images onto display layer 440 to present image light 441 to eyebox region 201. Processing logic 470 may be configured to drive one or more sensors (e.g. camera 477) of an eye-tracking system to capture eye-tracking data such as eye data 479. Eye data 479 may include images of an eye 203 occupying eyebox region 201. Processing logic 470 may be configured to generate a user notification in response to eye data 479. In an implementation, processing logic 470 drives near-eye display 440 to present the user notification to the eyebox region in a virtual image 443. In an implementation, processing logic 470 causes the user notification to be wirelessly transmitted to a wireless network in a wireless message 481. Wireless message 481 may be wirelessly transmitted by a wireless radio (not specifically illustrated) of head mounted device 400. The user notification of wireless message 481 may be transmitted to a computing device such as a smartwatch, smartphone, tablet, or otherwise.

Figure 5:
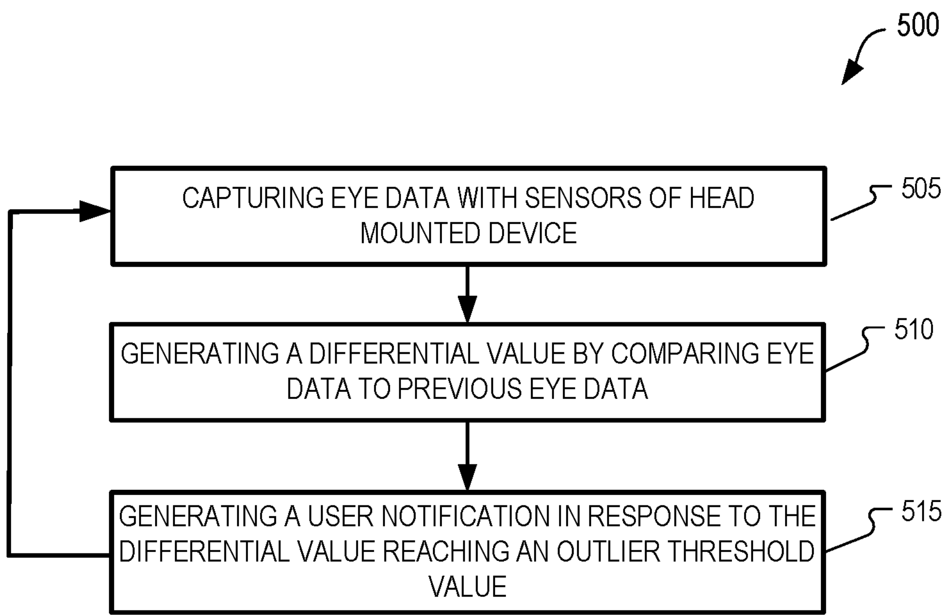
FIG. 5 illustrates a flow chart illustrating an example notification process, in accordance with aspects of the disclosure.

FIG. 5 illustrates a flow chart illustrating an example process 500, in accordance with implementations of the disclosure. The order in which some or all of the process blocks appear in process 500 should not be deemed limiting. Rather, one of ordinary skill in the art having the benefit of the present disclosure will understand that some of the process blocks may be executed in a variety of orders not illustrated, or even in parallel. All or a portion of process 500 may be executed by processing logic of a head mounted device. In some implementations, at least a portion of process 500 is executed by processing logic that is remote from the head mounted device (e.g. cloud processing).

In process block 505, eye data is captured with one or more sensors of a head mounted device. The one or more sensors are configured to sense an eyebox region (e.g. eyebox region 201). The sensors may include a camera (including an image sensor), photodiodes, ultrasound, and/or LIDAR units, for example.

The eye data may include one or more images of the eyebox region. The eye data may include at least one of a pupil size of an eye, speed of pupil dilation of the eye, a gaze direction of the eye, or eye-movement data. In some implementations, the eye data may be generated by performing image processing on one or more images of an eye. Processing logic 470 may perform image processing, in some implementations.

In process block 510, a differential value is generated by comparing the eye data to previous data. The previous data may include previous eye data from a specific user. The previous eye data may include at least one of a previous pupil size of an eye, previous speed of pupil dilation of the eye, a previous gaze direction of the eye, or previous eye-movement data. The previous eye data may be stored in a memory of the head mounted device or stored in a memory remote from the head mounted device. The previous data may be user-specific or aggregate health data that is not user-specific (e.g. data that is crowd-sourced). For example, user-specific data may be a previous pupil diameter measured by the head mounted device whereas aggregate health data may be an average pupil size of a given user group or demographic.

Figure 8:
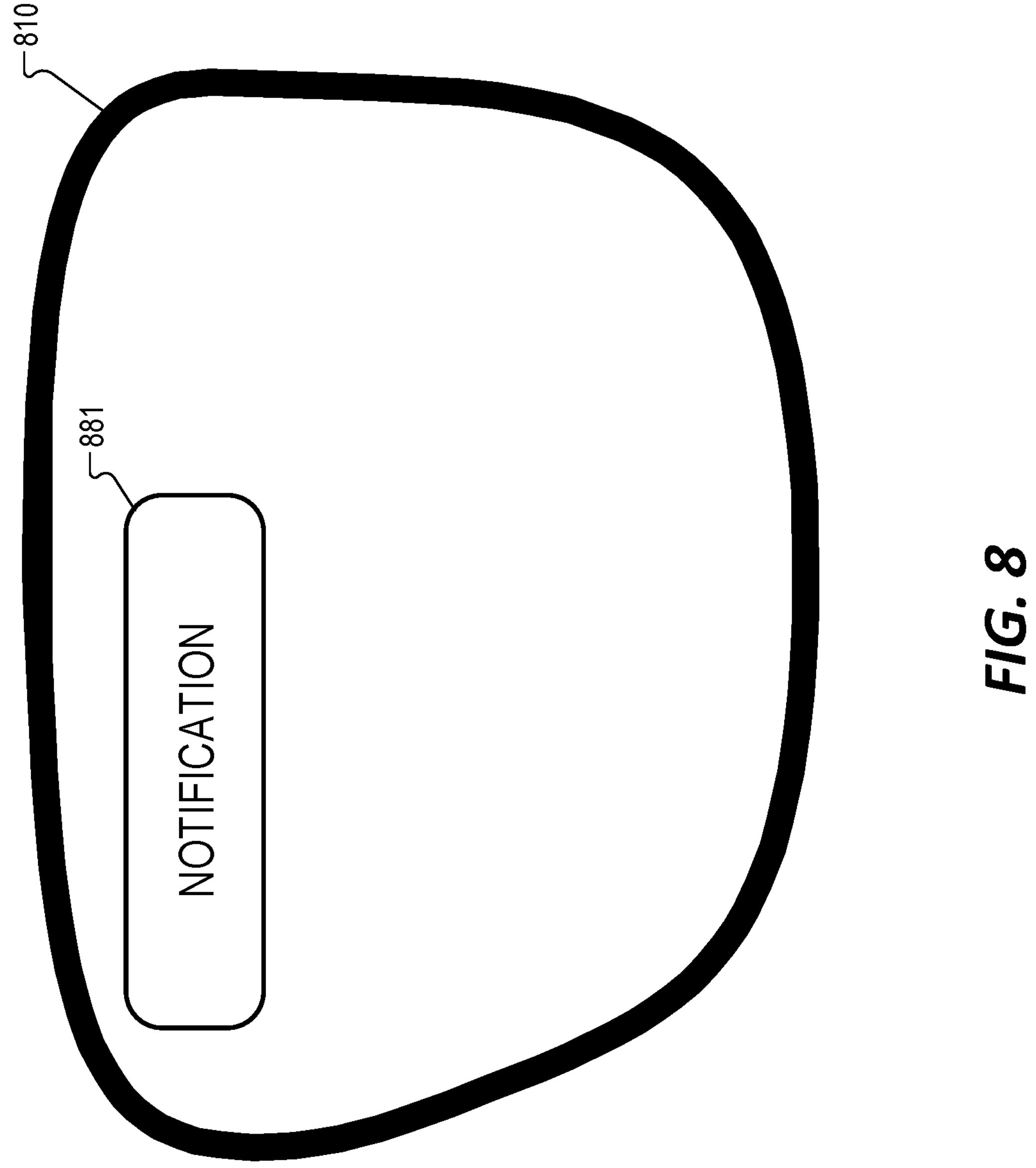
FIG. 8 illustrates an example user notification included in a virtual image that is presented to a user in a near-eye optical element that includes a near-eye display, in accordance with aspects of the disclosure.

In process block 515, a user notification is generated in response to the differential value reaching an outlier threshold value. In an implementation, generating the user notification includes wirelessly transmitting the user notification (e.g. user notification in wireless message 481 in FIG. 4) to a wireless network. The user notification may be a message to a user account, a doctor, or a parent, for example. In an implementation, generating the user notification includes driving a near-eye display (e.g. display 440 of FIG. 4) of the head mounted device to present the user notification to the user in a virtual image. FIG. 8 illustrates an example user notification 881 included in a virtual image that is presented to a user in a near-eye optical element 810 that includes a near-eye display. Process 500 may return to process block 505 after executing process block 515.

In an example implementation of process 500, camera 477 captures images of an eye 203 in eyebox region 201. Image processing is performed on the one or more images of the eye to determine a heart rate of a user of the head mounted device and the eye data includes the heart rate. The heart rate of a user can be generated by performing image processing on a series of images of an eye by analyzing the pupil diameter over time, for example. In another implementations, the heart rate of a user can be generated by performing image processing on a series of images of an eye by analyzing the size of blood vessels of the eye over time. In this technique, the expansion and contraction of the blood vessels corresponds to the heart rate. After the heart rate of the user is determined, it may be compared to a previous heart rate of the user stored in a memory. The previous heart rate of the user may have previously been determined by the head mounted device (or other wearable device) and stored in the memory. The differential value is generated by comparing the determined heart rate from the previously stored heart rate. Hence, if the determined heart rate was 200 beats-per-minute (bpm) and the previously stored heart rate was 160 bpm, the differential value may be 40 bpm. If the outlier threshold value is 20 bpm above 160 bpm, then the user notification may be generated since the 40 bpm differential value reaches the 20 bpm outlier threshold value. A heart rate of 200 bpm may be an indication of a health event or of hyper-aerobic activity, for example.

In another example implementation of process 500, camera 477 captures images of an eye 203 in eyebox region 201. Image processing is performed on the one or more images of the eye to determine a number of saccades in a fixed time period (e.g. in one minute) of a user of the head mounted device and the eye data includes the number of saccades in the fixed time period as eye-movement data. After the number of saccades in the fixed time period is determined, it may be compared to a previous number of saccades over the same fixed time period of the user stored in a memory. If the number of saccades over the same fixed time period exceeds an expected number of saccades in the fixed time period by the outlier threshold value, a user notification may be generated. Or, if the number of saccades over the same fixed time period is below an expected number of saccades in the fixed time period by the outlier threshold value, a user notification may be generated. An increase or decrease of saccades over a particular time period compared to an average amount of saccades or "normal" number of saccades may be indicative of a condition or a traumatic event (e.g. a concussion).

Process 500 may further include increasing a capture-rate of capturing the eye data in response to the differential value reaching the outlier threshold value. For example, a frame-rate of images captured by camera 477 may be increased in order to capture more frequent images of eyebox region 201 for further analysis.

In implementations of process 500, an eye brightness value of the eyebox region may be relevant to the eye data being captured. For example, in bright sunlight conditions, an eye brightness value of the eyebox region may be quite high and result in a smaller pupil diameter. The eye brightness value represents an intensity of light that is incident on the eyebox region. Camera 477 may output an eye brightness value based on pixel values of an image sensor in camera 477. In other implementations, one or more photodiodes included in a head mounted device may be directed to receive light from the eyebox region to measure the eye brightness value of the eyebox region. Comparing the captured eye data to previous eye data may be best when the eye data is captured under similar illumination levels (e.g. dark environments or bright environments).

Figure 6:
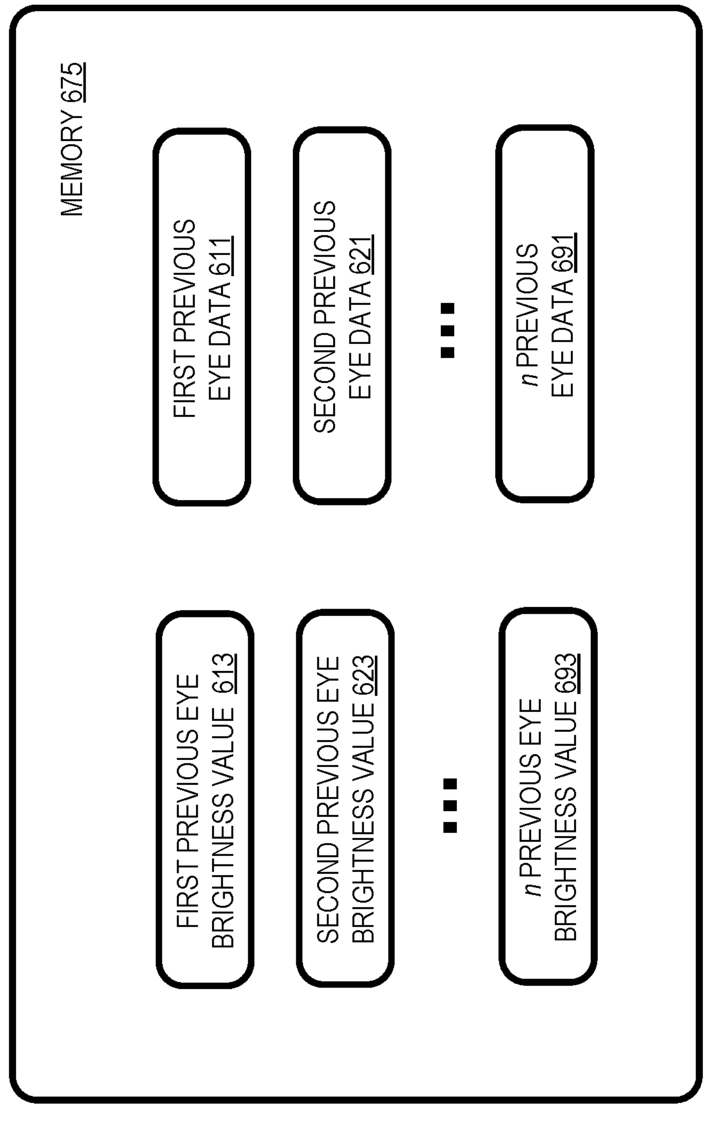
FIG. 6 illustrates example previous eye brightness values paired with previous eye data in a memory, in accordance with aspects of the disclosure.

FIG. 6 illustrates example previous eye brightness values paired with previous eye data in a memory 675, in accordance with implementations of the disclosure. In particular, a first previous eye brightness value 613 is paired with first previous eye data 611 and a second previous eye brightness value 623 is paired with second previous eye data 621. Memory 675 may include integer n number of previous eye brightness values 693 paired with n number of previous eye data 691. Thus, given a measured eye brightness value, previous eye data can be selected from memory 675 for a similar eye brightness value. By way of example illustration, a pupil diameter of eye data 611 may correspond with a very low eye brightness value 613. For example, a pupil diameter in eye data 611 may be large when the user is using the head mounted device in a darker environment. A pupil diameter in eye data 621 may be slightly smaller than the pupil diameter in eye data 621 when the eye brightness value 623 is higher than the darker environment of eye brightness value 613.

An implementation of process 500 may utilize a memory such as memory 675 to execute further operations including determining an eye brightness value of the eyebox region at approximately a same time as the eye data is captured where the eye brightness value represents a brightness of visible light on the eyebox region. In this case, generating the differential value may include comparing the eye data paired with the eye brightness value to previous eye data (e.g. data 611) paired with a previous eye brightness value (e.g. value 613) in a same range as the eye brightness value measured at the same time the eye data is captured. By way of example, the measured eye brightness value may be associated with the numerically closest previous eye brightness value stored in memory 675. The previous eye data paired with the numerically closest previous eye brightness value then becomes the previous eye data for the generating the differential value.

Figure 7:
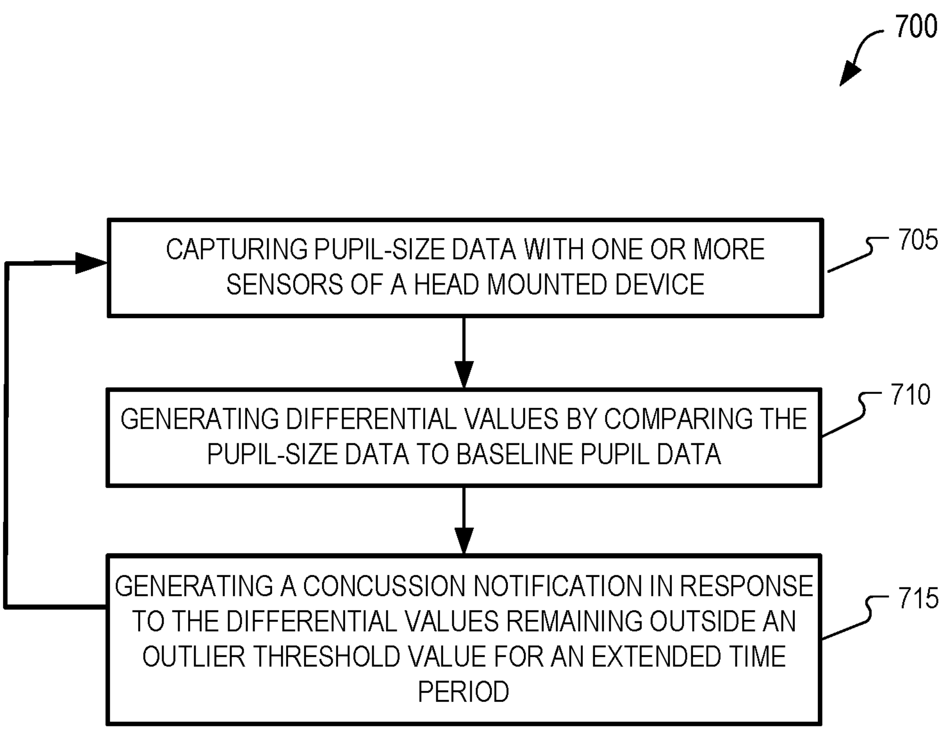
FIG. 7 illustrates a flow chart illustrating an example concussion notification process, in accordance with aspects of the disclosure.

FIG. 7 illustrates a flow chart illustrating an example concussion notification process 700, in accordance with implementations of the disclosure. The order in which some or all of the process blocks appear in process 700 should not be deemed limiting. Rather, one of ordinary skill in the art having the benefit of the present disclosure will understand that some of the process blocks may be executed in a variety of orders not illustrated, or even in parallel.

Concussions may result from sports or other activities. Pupils that are larger than normal (dilated pupils) may indicate a possible concussion. Or, pupils of different sized (e.g. the right pupil and the left pupil are different diameters) may indicate a possible concussion. Thus, a concussion of a user may be detected from measuring eye pupil size.

In process block 705, pupil-size data is captured with one or more sensors of a head mounted device. The one or more sensors are configured to sense the eyebox region. The pupil-size data may be determined by performing image processing techniques on images of eye data 479, for example.

In process block 710, differential values are generated by comparing the pupil-size data to baseline pupil data. The baseline pupil data may be specific to the user under certain light conditions or the baseline pupil data may be a crowd-sourced average pupil data, for example.

In process block 715, a concussion notification is generated in response to the differential values remaining outside an outlier threshold value for an extended time period. The outlier threshold value may be a larger pupil diameter or be expressed as a percentage increase of the baseline pupil data for a particular light condition. If the pupil remains much larger than expected for an extended period of time, the user may have experienced a concussion. The concussion notification may be delivered in a virtual image such as notification 881 in FIG. 8 or may be delivered via a message transmitted with a wireless radio of the head mounted device. The concussion notification may be transmitted to a computing device such as a smartwatch, smartphone, tablet, or otherwise.

In some implementations, both the right and left pupil diameter over a time period may be logged. A difference in pupil diameter between the right and left pupil (over a certain time period) may also generate a concussion notification.

Embodiments of the invention may include or be implemented in conjunction with an artificial reality system. Artificial reality is a form of reality that has been adjusted in some manner before presentation to a user, which may include, e.g., a virtual reality (VR), an augmented reality (AR), a mixed reality (MR), a hybrid reality, or some combination and/or derivatives thereof. Artificial reality content may include completely generated content or generated content combined with captured (e.g., real-world) content. The artificial reality content may include video, audio, haptic feedback, or some combination thereof, and any of which may be presented in a single channel or in multiple channels (such as stereo video that produces a three-dimensional effect to the viewer). Additionally, in some embodiments, artificial reality may also be associated with applications, products, accessories, services, or some combination thereof, that are used to, e.g., create content in an artificial reality and/or are otherwise used in (e.g., perform activities in) an artificial reality. The artificial reality system that provides the artificial reality content may be implemented on various platforms, including a head-mounted display (HMD) connected to a host computer system, a standalone HMD, a mobile device or computing system, or any other hardware platform capable of providing artificial reality content to one or more viewers.

The term "processing logic" (e.g. processing logic 470) in this disclosure may include one or more processors, microprocessors, multi-core processors, Application-specific integrated circuits (ASIC), and/or Field Programmable Gate Arrays (FPGAs) to execute operations disclosed herein. In some embodiments, memories (not illustrated) are integrated into the processing logic to store instructions to execute operations and/or store data. Processing logic may also include analog or digital circuitry to perform the operations in accordance with embodiments of the disclosure.

A "memory" or "memories" (e.g. memory 475 and/or memory 675) described in this disclosure may include one or more volatile or non-volatile memory architectures. The "memory" or "memories" may be removable and non-removable media implemented in any method or technology for storage of information such as computer-readable instructions, data structures, program modules, or other data. Example memory technologies may include RAM, ROM, EEPROM, flash memory, CD-ROM, digital versatile disks (DVD), high-definition multimedia/data storage disks, or other optical storage, magnetic cassettes, magnetic tape, magnetic disk storage or other magnetic storage devices, or any other non-transmission medium that can be used to store information for access by a computing device.

Networks may include any network or network system such as, but not limited to, the following: a peer-to-peer network; a Local Area Network (LAN); a Wide Area Network (WAN); a public network, such as the Internet; a private network; a cellular network; a wireless network; a wired network; a wireless and wired combination network; and a satellite network.

Communication channels may include or be routed through one or more wired or wireless communication utilizing IEEE 802.11 protocols, BlueTooth, SPI (Serial Peripheral Interface), $I^2C$ (Inter-Integrated Circuit), USB (Universal Serial Port), CAN (Controller Area Network), cellular data protocols (e.g. 3G, 4G, LTE, 5G), optical communication networks, Internet Service Providers (ISPs), a peer-to-peer network, a Local Area Network (LAN), a Wide Area Network (WAN), a public network (e.g. "the Internet"), a private network, a satellite network, or otherwise.

A computing device may include a desktop computer, a laptop computer, a tablet, a phablet, a smartphone, a feature phone, a server computer, or otherwise. A server computer may be located remotely in a data center or be stored locally.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

A tangible non-transitory machine-readable storage medium includes any mechanism that provides (i.e., stores) information in a form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. A method of operating a head mounted device, the method comprising:

capturing eye data for a user with one or more sensors of the head mounted device, wherein the one or more sensors are configured to sense an eyebox region;

generating a differential value by comparing the eye data to previous data, the previous data including at least one of a pupil size previously captured for an eye of one or more users, speed of pupil dilation previously captured for the eye of the one or more users, a gaze direction previously captured for the eye of the one or more users, or eye-movement data previously captured for the eye of the one or more users, and wherein the differential value is based on at least one a differences in pupil size, a difference in pupil dilation speed, a difference in gaze direction, or a difference in eye-movement; and generating a user notification in response to the differential value reaching an outlier threshold value.

2. The method of claim 1, wherein the eye data includes at least one of a pupil size of an eye, speed of pupil dilation of the eye, a gaze direction of the eye, or eye-movement data.

3. The method of claim 1, wherein the sensing the eyebox region includes capturing one or more images of an eye.

4. The method of claim 3 further comprising:

performing image processing on the one or more images of the eye to determine a heart rate of the user of the head mounted device, wherein the differential value is further based on an analysis of the heart rate of the user.

5. The method of claim 1, further comprising:

determining, based on the eye data, a number of saccades in a fixed time period;

wherein the differential value is further based on an analysis of the number of saccades in the fixed time period.

6. The method of claim 1 further comprising:

increasing a capture-rate of capturing the eye data in response to the differential value reaching the outlier threshold value.

7. The method of claim 1 further comprising:

determining an eye brightness value of the eyebox region at approximately a same time as the eye data is captured, wherein the eye brightness value represents a brightness of visible light on the eyebox region, wherein generating the differential value includes comparing the eye data paired with the eye brightness value to previous eye data paired with a previous eye brightness value in a same range as the eye brightness value, the previous eye brightness value captured while the previous eye data is measured, and wherein the previous eye data and the previous eye brightness value is included in the previous data.

8. The method of claim 1, wherein generating the user notification includes driving a near-eye display of the head mounted device to present the user notification to a user of the head mounted device in a virtual image.

9. The method of claim 1, wherein generating the user notification includes wirelessly transmitting the user notification to a wireless network.

10. The method of claim 1, wherein the previous data is user-specific eye data that was derived from previously captured eye data for the user.

11. The method of claim 1, wherein the previous data is aggregate health data that is not user-specific.

12. A computer-readable storage medium storing instructions, for operating a head mounted device, the instructions, when executed by a computing system, cause the computing system to perform a process comprising:

capturing eye data for a user with one or more sensors of the head mounted device, wherein the one or more sensors are configured to sense an eyebox region;

generating differential values by comparing the eye data to previous data, the previous data including at least one of a pupil size previously captured for an eye of one or more users, speed of pupil dilation previously captured for the eye of the one or more users, a gaze direction previously captured for the eye of the one or more users, or eye-movement data previously captured for the eye of the one or more users, and wherein the differential value is based on at least one a differences in pupil size, a difference in pupil dilation speed, a difference in gaze direction, or a difference in eye-movement; and generating a concussion notification in response to the differential values remaining outside an outlier threshold value for an extended time period.

13. A head mounted device comprising:

an eye-tracking system including one or more sensors configured to capture eye data from an eyebox region of the head mounted device; and processing logic configured to:

capture eye data for a user with the eye-tracking system of the head mounted device;

generate a differential value by comparing the eye data to previous data, the previous data including at least one of a pupil size previously captured for an eye of one or more users, speed of pupil dilation previously captured for the eye of the one or more users, a gaze direction previously captured for the eye of the one or more users, or eye-movement data previously captured for the eye of the one or more users, and wherein the differential value is based on at least one a differences in pupil size, a difference in pupil dilation speed, a difference in gaze direction, or a difference in eye-movement; and generate a user notification in response to the differential value reaching an outlier threshold value.

14. The head mounted device of claim 13, wherein the eye data includes at least one of a pupil size of an eye, speed of pupil dilation of the eye, a gaze direction of the eye, or eye-movement data.

15. The head mounted device of claim 13, wherein the sensing the eyebox region includes capturing one or more images of an eye.

16. The head mounted device of claim 15, wherein the processing logic is further configured to:

performing image processing on the one or more images of the eye to determine a heart rate of the user of the head mounted device, wherein the differential value is further based on an analysis of the heart rate of the user.

17. The head mounted device of claim 13, wherein the processing logic is further configured to:

determine, based on the eye data, a number of saccades in a fixed time period;

wherein the differential value is further based on an analysis of the number of saccades in the fixed time period.

18. The head mounted device of claim 13, wherein the processing logic is further configured to:

increase a capture-rate of capturing the eye data in response to the differential value reaching the outlier threshold value.

19. The head mounted device of claim 13 further comprising:

a near-eye display configured to present a virtual image to the eyebox region, wherein generating the user notification includes the processing logic driving the near-eye display of the head mounted device to present the user notification to the eyebox region in the virtual image.

20. The head mounted device of claim 13, wherein generating the user notification includes wirelessly transmitting the user notification to a wireless network.

* * * * *